United States Patent [19]

Cary, Jr.

[11] Patent Number: 5,272,139
[45] Date of Patent: Dec. 21, 1993

[54] AMELIORATION OR ELIMINATION OF POSTOPERATIVE PAIN

[76] Inventor: George R. Cary, Jr., 1411 Eleanor St., New Orleans, La. 70115

[21] Appl. No.: 707,309

[22] Filed: May 29, 1991

Related U.S. Application Data

[63] Continuation of Ser. No. 483,991, Feb. 22, 1990, abandoned, which is a continuation of Ser. No. 74,994, Jul. 17, 1987, abandoned, which is a continuation-in-part of Ser. No. 900,683, Aug. 27, 1986, abandoned.

[51] Int. Cl.$^5$ .............................................. A61K 31/56
[52] U.S. Cl. .................................. 514/171; 514/177; 514/178; 514/179; 514/180; 514/816; 514/817
[58] Field of Search ............... 514/171, 178, 179, 180, 514/177

[56] References Cited

U.S. PATENT DOCUMENTS

| | | | |
|---|---|---|---|
| 3,337,400 | 8/1967 | Smith | 514/171 |
| 4,025,645 | 5/1977 | Jelenko | 514/857 |
| 4,213,979 | 7/1980 | Levine | 514/171 |
| 4,434,179 | 2/1984 | Kobayashi et al. | 514/927 |

FOREIGN PATENT DOCUMENTS 87207163  10/1989  European Pat. Off.

OTHER PUBLICATIONS

British Journal of Ophthalmology, vol. 64, 1980, pp. 43-45.
The Journal of Foot Surgery, vol. 22, No. 3, 1983, pp. 187-191.
Oral Surg., vol. 40, 1975, pp. 594-598.
The Journal of Foot Surgery, vol. 24, No. 2, 1985, pp. 142-147.
Merck Index (1983), 10th Ed., #2510, #5310, #7661 and #2331.
Stedman's Medical Dictionary, Twentieth Ed., The Williams of Wilkins Co., Baltimore, (1961), pp. 767, 771 and 772.
Webster's II New Riverside University Dictionary, The Riverside Publishing Co., Boston, (1984).

Primary Examiner—Frederick E. Waddell
Assistant Examiner—T. J. Criares
Attorney, Agent, or Firm—Cushman, Darby & Cushman

[57] ABSTRACT

Following completion of an operative procedure, the topical application of a cortisone preparation into the area of a postoperative wound is useful in ameliorating or eliminating postoperative pain. The postoperative wound can be treated with a local anesthetic agent prior to or during application of the cortisone preparation. The raw surgical surfaces of the wound are doused once with the cortisone preparation, for example, by direct spray with an atomizer or by irrigation with a syringe and needle. The cortisone is not irrigated out with saline following its application. Normal healing takes place.

11 Claims, No Drawings

AMELIORATION OR ELIMINATION OF POSTOPERATIVE PAIN

This is a continuation of application Ser. No. 07/483,991, filed on Feb. 22, 1990, which was abandoned upon the filing hereof which is a continuation of Ser. No. 07/074,994 filed Jul. 17, 1987, which is a continuation-in-part of Ser. No. 900,683, filed Aug. 27, 1986, both now abandoned.

The present invention relates to a method of ameliorating or eliminating the pain experienced by patients recovering from surgery.

Heretofore, the prior art has not disclosed an analgesic agent which is effective in reducing or eliminating postoperative pain without also producing detrimental side effects such as, for example drowsiness or nausea.

Among the objects of the present invention is the provision of a treatment which, alleviates postoperative pain without such detrimental side effects. The foregoing as well as still further objects of the present invention will be more fully understood from the following description.

According to the present invention, the surface application of a cortisone preparation into the area of a postoperative wound is useful in reducing or eliminating postoperative pain. In accordance with the procedure of the present invention, and following completion of an operative procedure, the raw surgical surfaces of the postoperative wound are doused once with the said corticosteroid preparation. A small amount of the material is applied to the surfaces of the wound in any convenient fashion, for example, by direct spray using an atomizer or by irrigation using a syringe and needle. The corticosteroid preparation is not irrigated out with saline following its application. The wound is closed in a routine fashion. Excess corticosteroid preparation drains out of the wound in the usual manner. Normal healing takes place.

Further, in accordance with the invention, the raw surgical surfaces of the postoperative wound can be treated with a corticosteroid preparation and a local anesthetic or other pain relieving medication.

It has been found helpful to the patient to apply a local anesthetic agent, preferably a long acting anesthetic agent, such as Marcaine, Xylocaine, Lidocaine, Novacaine, and the like, to the postoperative wound separately or along with the corticosteroid for immediate elimination of pain during the first several hours after the operation, the period of time that the corticosteroid is weakest in its effect.

The effect of the surface application of a corticosteroid preparation into the area of a postoperative wound, according to the invention, is dramatic. Postoperative pain is decreased significantly or eliminated. In cases of bilateral surgery when, for comparative purposes, one side is treated with a corticosteroid preparation while the other side is left untreated, the patient undergoes a painful postoperative recovery on the untreated side while experiencing no pain of significance on the treated side.

Any readily available corticosteroid preparation which is topically applicable can be used for present purposes. Celestone Suspension (sold as Celestone Soluspan by Schering Corporation, Kenilworth, N.J.; each ml of Celestone Soluspan containing 3.0 mg betamethasone sodium phosphate and 3.0 mg beta-methasone acetate, for a total of 6.0 mg beta-methasone per ml of Celestane Soluspan) is preferred, although other corticosteroid preparations which are sprayable or otherwise suitable for topical application may be used. Celestone Suspension is a suspension brand of sterile beta-methasone sodium phosphate and beta-methasone acetate USP.

The amount of corticosteroid applied to the surgical wound can be varied and will depend on such factors as the scope and severity of the wound. The effective amount of corticosteroid to be used can be readily ascertained for any specific situation.

Corticosteroid acts as an anti-inflammatory, reducing tissue swelling and thereby reducing painful pressure on surrounding nerves; in addition, corticosteroid acts directly on the severed ends of nerves. Research is being carried out to determine further the mechanism of action of corticosteroid when applied to the surface of surgical wounds.

The amount of local anesthetic or other pain relieving medication applied to the surgical wound can be varied and will depend on such factors as the scope and severity of the wound. The effective amount of anesthetic to be used can be readily ascertained for any specific situation.

The anesthetic can be applied to the surgical wound along with the corticosteroid or applied separately depending upon circumstances. The anesthetic can be applied to the surgical surfaces of the wound prior to application of the corticosteroid preparation. Any readily available local anesthetic preparation which is topically applicable can be used for present purposes. Representative examples of anesthetics that can be used include Marcaine, Xylocaine, Lidocaine, Novocain, and the like. The anesthetic can be applied to the surgical wound in any manner, for example, spraying, irrigating, sprinkling, or any appropriate mode available.

The present invention is illustrated in detail in the following examples. These examples are included for illustrative purposes only and should not be considered to limit the present invention.

EXAMPLE 1

Bilateral Keller Bunionectomy

The soft tissue is excised over the medial aspect of the first MP joint of the great toe. The excision is continued through the soft tissues to the first joint of the great toe. The proximal phalanx of the great toe is removed, as well as the bunion over the medial portion of the distal aspect of the first metatarsal. Raw bony areas are left exposed, as well as the excised soft tissues.

A corticosteroid preparation, for example, Celestone Suspension, is applied to the surface of the raw surgical wound, either by direct spray using an atomizer or by irrigation using a syringe and needle. When spraying, 1 cc of the corticosteroid preparation is applied to the raw surgical tissues; when irrigating, 1.5 cc to 2 cc are applied. The material is used on only one occasion. The corticosteroid preparation is not irrigated out with saline following its application. The wound is closed in a routine fashion. Excess corticosteroid preparation drains out of the wound by gravity. Normal healing takes place.

The patient commonly notes some discomfort in the recovery room when only corticosteroid is used. However, following recovery from the general anaesthetic, minimal discomfort in the surgical area is experienced. Utilizing pressure dressings over the feet, the patient is immediately able to ambulate about the room and otherwise.

When, for comparative purposes, one foot is treated with a corticosteroid preparation while the other foot is left untreated, the patient's response is dramatic. The patient complains significantly about the untreated foot and usually questions the surgeon as to what was done differently in the two extremities.

EXAMPLE 2

Dupuytren's Excision of the Palm of the Hand

An excessive growth of subcutaneous fibrous tissue is removed from the palm of the hand, leaving a valley of exposed surgical tissues. The raw surfaces of the surgical tissues are doused once with, usually, less than 1 cc of a corticosteroid preparation, for example, Celestone Suspension or a combination of Marcaine and Celestone mixed usually in equal volumes. The material is applied to the raw surgical surfaces of the wound either by direct spray using an atomizer or by irrigation using a syringe and needle. The corticosteroid preparation is not irrigated out with saline following its application. The wound is closed routinely. Excess corticosteroid preparation drains out of the wound in the usual manner. Normal healing takes place.

Although taking a bone graft from the ileum is a procedure which usually entails a painful postoperative recovery, the application of a corticosteroid preparation to the raw surgical surfaces of the postoperative wound eliminates significant postoperative discomfort in the area of the bone graft site.

The invention having been described, it will be appreciated by those skilled in the art, that various modifications can be made within the scope of the following claims.

What is claimed is:

1. A method for the reduction or elimination of postoperative pain caused by a postoperative wound, which comprises the surface application by spraying or irrigating the raw surgical surfaces of the wound with a pain reducing amount of a corticosteroid preparation which functions topically to reduce pain, and thereafter closing said wound whereby healing of the wound occurs in a normal manner.

2. The method of claim 1, wherein the corticosteroid preparation is applied to the raw surgical surfaces of the postoperative wound by direct spray using an atomizer.

3. The method of claim 1, wherein the corticosteroid preparation is applied to the raw surgical surfaces of the postoperative wound by irrigation using a syringe and needle.

4. The method of claim 1, which comprises the surface application of less than 3 cc of corticosteroid preparation to the raw surgical surfaces of the postoperative wound.

5. The method of claim 1, wherein the corticosteroid preparation comprises a suspension of betamethasone acetate and beta-methasone sodium phosphate.

6. A method according to claim 1 which further comprises the surface application of an effective amount of a local anesthetic to the surgical surfaces of the postoperative wound for the immediate elimination of pain during the first several hours after the operation.

7. A method according to claim 1 wherein a local anesthetic and corticosteroid are applied to the wound at approximately the same time.

8. A method according to claim 7 wherein a mixture comprising a local anesthetic and corticosteroid is applied to the wound.

9. A method according to claim 1 wherein said corticosteroid preparation contains a local anesthetic.

10. A method according to claim 6 wherein said anesthetic is one of Marcaine, Lidocaine, and Novocain.

11. A method according to claim 6 wherein said anesthetic is applied to the surgical surfaces prior to application of corticosteroid.

* * * * *